United States Patent
Kraus (10) Patent No.: US 10,925,217 B2
(45) Date of Patent: Feb. 23, 2021

(54) BALER WITH DRY MATTER CONTENT DETECTION SYSTEM

(71) Applicant: Deere & Company, Moline, IL (US)

(72) Inventor: Timothy J. Kraus, Blakesburg, IA (US)

(73) Assignee: DEERE & COMPANY, Moline, IL (US)

( * ) Notice: Subject to any disclaimer, the term of this patent is extended or adjusted under 35 U.S.C. 154(b) by 298 days.

(21) Appl. No.: 15/988,910

(22) Filed: May 24, 2018

(65) Prior Publication Data

US 2019/0098836 A1    Apr. 4, 2019

Related U.S. Application Data

(60) Provisional application No. 62/566,784, filed on Oct. 2, 2017, provisional application No. 62/566,855, filed on Oct. 2, 2017.

(51) Int. Cl.
*A01F 15/08* (2006.01)
*A01F 15/07* (2006.01)
(Continued)

(52) U.S. Cl.
CPC .......... *A01F 15/0833* (2013.01); *A01F 15/07* (2013.01); *A01F 15/106* (2013.01);
(Continued)

(58) Field of Classification Search
CPC .... A01F 15/07; A01F 15/106; A01F 15/0833; A01F 2015/0893; A01F 2015/0891; G01G 19/08; G01B 5/08; G01N 33/02
See application file for complete search history.

(56) References Cited

U.S. PATENT DOCUMENTS 2,796,825 A    6/1957  Kriegbaum et al.
5,384,436 A    1/1995  Pritchard
(Continued)

FOREIGN PATENT DOCUMENTS

| EP | 1029440 A1 | 8/2000 |
| EP | 2446731 A1 | 5/2012 |
| EP | 3031317 A1 | 6/2016 |

OTHER PUBLICATIONS

European Patent Office Extended Search Report for Application No. 18197533.5 dated Mar. 6, 2019 (8 pages).
(Continued)

*Primary Examiner* — Jimmy T Nguyen
(74) *Attorney, Agent, or Firm* — Michael Best & Friedrich LLP (57) ABSTRACT

A baler for baling crop material, the baler including a frame, a feed assembly coupled to the frame, and a forming chamber where the forming chamber includes an inlet through which crop material may pass into the forming chamber. The baler also includes a moisture sensor configured to detect the moisture content of crop material passing into the forming chamber, a plurality of force sensors configured to detect the mass of a bale positioned within the forming chamber, and a controller in operable communication with the moisture sensor and the plurality of force sensors, and wherein the controller is configured to calculate the mass of dry matter contained within a bale positioned within the forming chamber.

14 Claims, 4 Drawing Sheets

(51) Int. Cl.
  *A01F 15/10* (2006.01)
  *G01B 5/08* (2006.01)
  *G01N 33/02* (2006.01)
  *G01G 19/08* (2006.01)

(52) U.S. Cl.
  CPC .............. *G01B 5/08* (2013.01); *G01G 19/08* (2013.01); *G01N 33/02* (2013.01); *A01F 2015/0891* (2013.01)

(56) References Cited

U.S. PATENT DOCUMENTS

| | | |
|---|---|---|
| 6,378,276 B1 | 4/2002 | Dorge et al. |
| 7,703,391 B2 | 4/2010 | Duenwald et al. |
| 8,326,563 B2 | 12/2012 | Kraus |
| 9,182,269 B2 | 11/2015 | Kraus |
| 9,297,688 B2 | 3/2016 | Posselius et al. |
| 9,854,744 B2 | 1/2018 | Smith |
| 2004/0245028 A1 | 12/2004 | Viaud et al. |
| 2009/0217827 A1* | 9/2009 | Duenwald ........... A01F 15/0715 100/88 |
| 2012/0103207 A1* | 5/2012 | Kraus ................. A01F 15/0816 100/45 |
| 2016/0165803 A1* | 6/2016 | Smith ................... G05B 15/02 700/275 |
| 2016/0187185 A1 | 6/2016 | Smith |

OTHER PUBLICATIONS

European Patent Office Extended Search Report for Application No. 18197490.8 dated Mar. 6, 2019 (8 pages).

\* cited by examiner

BALER WITH DRY MATTER CONTENT DETECTION SYSTEM

CROSS-REFERENCE TO RELATED APPLICATIONS

This application claims priority to U.S. Provisional Patent Application No. 62/566,784 filed on Oct. 2, 2017 and U.S. Provisional Patent Application No. 62/566,855 filed on Oct. 2, 2017, the contents of both of which are incorporated herein by reference.

FIELD OF THE DISCLOSURE

The present disclosure relates to a baler and more specifically to a baler having a system for measuring and adjusting the amount of dry matter in a particular bale.

BACKGROUND

Typically, bales of crop material are placed in feeders so that a group of animals are allowed to consume the bale as feed. When feeding, only the dry matter or DM of a bale provides nutrition to the animal. However, the mass of the bale includes both DM and water or moisture content. As such, the weight of the bale does not determine how much nutrition is being provided to the animals.

SUMMARY

In one implementation, a system including a baler configured to produce a bale having a predetermined dimension, a mass sensor configured to measure a total mass of the bale, a bale-dimension sensor configured to measure a dimension of the bale, a moisture sensor configured to measure a moisture content of the bale, and a controller. Where the controller is configured to calculate an actual dry matter mass of the bale, compare a desired dry matter mass to the actual dry matter mass of the bale, and adjust the predetermined dimension based at least in part on the comparison of the desired dry matter mass to the actual dry matter mass of the bale.

In another implementation, a baler for baling crop material, the baler including a frame, a forming chamber configured to form a bale therein, where the forming chamber includes an inlet through which crop material may pass into the forming chamber, a moisture sensor configured to detect a moisture content of the bale, one or more mass sensors configured to detect a total mass of the bale, and a controller in operable communication with the moisture sensor and the one or more mass sensors, and where the controller is configured to calculate an actual dry matter mass of the bale.

In another implementation, a method of forming a bale with a baler having a controller, the method including receiving a signal indicating the moisture content of the bale, receiving a signal indicating the total mass of the bale, calculating the actual dry matter mass of the bale based at least in part on the moisture content of the bale and the total mass of the bale, comparing the actual dry matter mass of the bale to a desired dry matter mass of the bale, and adjusting a first attribute of the bale based at least in part on the comparison of the actual dry matter mass and the desired dry matter mass.

In another implementation, a system including a baler configured to produce a bale having a predetermined attribute, a force sensor configured to detect a total mass of the bale, a moisture sensor configured to measure a moisture content of the bale, and a controller. Where the controller is configured to calculate the actual dry matter mass of the bale based at least in part on the total mass of the bale and the moisture content of the bale, compare a desired dry matter mass to the actual dry matter mass, and adjust the predetermined attribute for a successive bale based at least in part on the comparison of the desired dry matter mass and the actual dry matter mass.

Other aspects of the disclosure will become apparent by consideration of the detailed description and accompanying drawings.

DETAILED DESCRIPTION

Before any embodiments of the disclosure are explained in detail, it is to be understood that the disclosure is not limited in its application to the details of the formation and arrangement of components set forth in the following description or illustrated in the accompanying drawings. The disclosure is capable of supporting other implementations and of being practiced or of being carried out in various ways.

The disclosure relates to balers and more particularly to balers having a control system configured to calculate the mass of dry matter (DM) contained in a particular bale. More specifically, the baler includes a controller using various sensors to determine the volume and weight of the current bale in addition to the average moisture level of the crop material comprising the bale. Together, the controller uses the collected data to calculate the mass of DM contained in the current forming bale and/or the volume or mass the bale must achieve to produce a desired mass of DM therein. By calculating the mass of DM in the bale, the user is able to more accurately assess the nutritional value contained in the bale. More specifically, only the DM of a bale provides nutritional value to animals as feed. Water or moisture, the other component contributing to the weight of the bale, provides no nutritional value. Therefore, weight alone is insufficient to determine the amount of nutrition a particular bale may provide. As such, the disclosed embodiments remove this uncertainty by determining what percentage of the bale's weight is water and what percentage of the bale's weight is nutritionally valuable DM.

Figure 1:
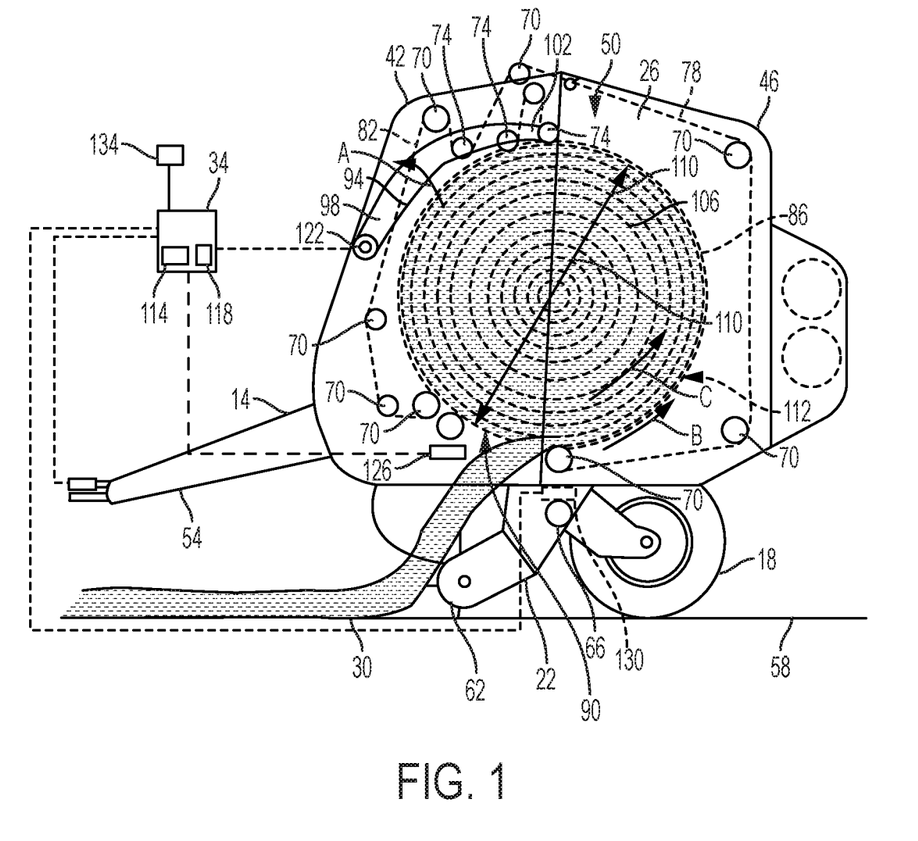
FIG. 1 is a side view of a round baler with a dry matter content detection system.

Referring to FIG. 1, a baler 10 includes a frame 14, a set of wheels 18 mounted to the frame 14, and a feed system 22. The baler 10 also includes a bale forming system 26 to collect and process crop material 30 provided by the feed system 22, and a controller 34 to monitor and direct the baling operation. In the illustrated implementation, the baler 10 is a round baler for creating finished bales 106 of a crop, such as hay, straw, or other biomasses.

In the illustrated implementation, the frame 14 of the baler 10 includes a forward housing 42 and a discharge gate 46 pivotably coupled to the forward housing 42 to define a volume 50 therebetween. During use, the discharge gate 46 is pivotable with respect to the forward housing 42 between a closed position (see FIG. 1), in which the volume 50 is completely enclosed by the discharge gate 46 and forward housing 42, and an open position (not shown), in which the discharge gate 46 is pivoted away from the forward housing 42 and the volume 50 is accessible from the outside.

The frame 14 of the baler 10 also includes a tow bar or tongue 54 extending from the forward housing 42 and connectable to a towing vehicle (not shown), such as an agricultural tractor or other driven vehicle. The baler 10 may also include a power takeoff shaft (not shown) connectable to the towing vehicle to transmit a rotating drive force from the towing vehicle to various components of the baler 10. In other implementations, the baler 10 may have a dedicated power supply and/or prime mover (not shown), such as an engine, motor, battery, fuel cell, etc., for driving the wheels 18 and for driving and/or powering the various components of the baler 10.

As shown in FIG. 1, the feed system 22 is configured to pick up windrowed crop material 30 from a support surface 58 (e.g., from a field) and convey the crop material 30 to the bale forming system 26. In the illustrated implementation, the feed system 22 includes a pickup assembly 62 for collecting the crop material 30 from the support surface 58, and a delivery assembly 66 for directing a continuous stream of crop material 30 evenly along the entire width of the bale forming system 26.

Illustrated in FIG. 1, the bale forming system 26 is generally a round baling system as is customary in the art. The bale forming system 26 includes a first set of rollers 70, a second set of rollers 74, and one or more belts 78 supported by the first and second sets of rollers 70, 74 to define a belt path 82. The size and shape of the belts 78 extending along the belt path 82 furthermore defines a variable size forming chamber 86 within the volume 50 having an inlet 90 positioned proximate the delivery system 66. During use, the second set of rollers 74 moves with respect to the first set of rollers 70 to change the size of the forming chamber 86.

In the illustrated implementation, the second set of rollers 74 are mounted for rotation on a tension arm 94. The tension arm 94, in turn, includes an elongated member having a first end 98 pivotably coupled to the forward housing 42, and a second end 102 opposite the first end 98. In the illustrated implementation, each roller 74 of the second set of rollers is rotatably coupled to the tension arm 94 proximate the second end 102 such that the rotational motion of the tension arm 94 causes the second set of rollers 74 to move along an arcuate path within the volume 50. While the illustrated implementation includes a tension arm 94 that is pivotally mounted to the forward housing 42, it is to be understood that in alternative implementations the tension arm 94 may be mounted for translational motion with respect to the first set of rollers 70. Still further, the tension arm 94 may be configured to include a combination of both rotational and translational movement.

During use, the tension arm 94 and second set of rollers 74 are moveable with respect to the first set of rollers 70 between a first position, in which the rollers 74 are located a first distance from the inlet 90 of the forming chamber 86, and a second position, in which the rollers 74 are positioned a second distance from the inlet 90 greater than the first distance. Generally speaking, the rotational orientation of the tension arm 94 is dictated by the bale diameter 110 of the bale 106 positioned within the forming chamber 86. In the illustrated implementation, at least one roller 74 of the second set of rollers 74 rests against and engages the outer annular surface 112 of the bale 106, acting as a follower. The at least one roller 74 remains in contact with the outer surface 112 of the bale 106 such that changes in bale diameter 110 cause changes in tension arm 94 position. As such, the angular orientation of the tension arm 94 is representative of the bale diameter 110 of the bale 106 positioned in the forming chamber 86.

The tension arm 94 also includes a biasing member (not shown) to bias the tension arm 94 toward the first position and maintain tension in the belts 78. In some implementations, the biasing member may include a spring, gas shock, and the like providing a continuous pressure toward the first position. However, in alternative implementations the biasing member may include a hydraulic cylinder, linear actuator, and the like to allow the user to more actively direct the movement of the tension arm 94 within the volume 50.

During the baling process, crop material 30 is fed into the forming chamber 86 through the inlet 90 by the delivery assembly 66 of the feed system 22, creating a cylindrically shaped bale 106 therein. The bale 106, in turn, is in contact with and supported along at least a portion of its outer annular surface 112 by the belts 78 which are held under tension by the tension arm 94 (described above) via the rollers 74. During use, the belts 78 are circulated around the belt path 82 in direction B, imparting a rotation to the bale 106 in direction C as is customary in the art. Furthermore, the tension in the belts 78 is configured to apply a radially inward compressive force on the annular wall 112 of the bale 106, compressing the crop material 30 contained therein.

As crop material 30 is continuously fed through the inlet 90 and into the forming chamber 86, the rotational motion of the bale 106 results in crop material 30 being deposited along the bale's outer annular surface 112 forming a sort of expanding spiral pattern (see FIG. 1) as is known by those ordinarily skilled in the art. Similarly, the tension within the belts 78 helps compact the newly applied crop material 30 onto the outer annular surface 112 of the bale 106. As a result, the forming bale 106 increases in diameter 110 as the baling process progresses.

As the bale 106 increases in diameter 110, the at least one roller 74 of the tension arm 94 in contact with the bale 106 acts as a follower, remaining in contact with the outer surface 112 of the growing bale 106 and causing the tension arm 94 to rotate in direction A away from the first position and toward the second position. As described above, the motion of the tension arm 94, in turn, causes the size of the forming chamber 86 to increase. The bale 106 and chamber 86 continue to increase in size together until the desired bale diameter 110 is reached. Once complete, the bale 106 may be wrapped as is well known in the art, and ejected from the rear of the baler 10 via the discharge gate 46.

After ejecting the completed bale 106, the tension arm 94 returns to the first position, thereby reducing the size of the forming chamber 86 to its original starting dimensions. The user may then begin the baling process for a subsequent bale.

Figure 2:
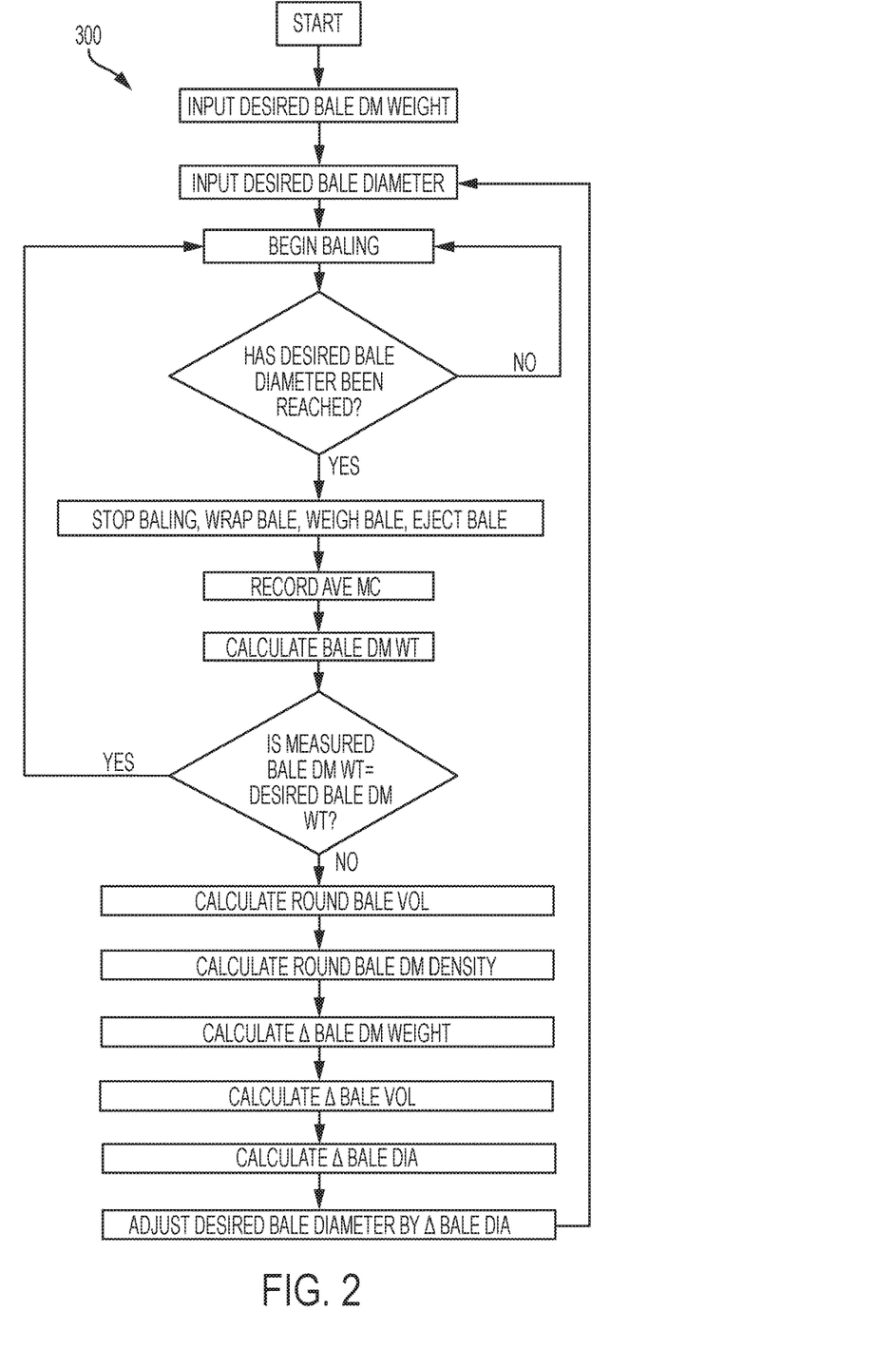
FIG. 2 is a diagram of a first mode of operation of the baler of FIG. 1.
Figure 3:
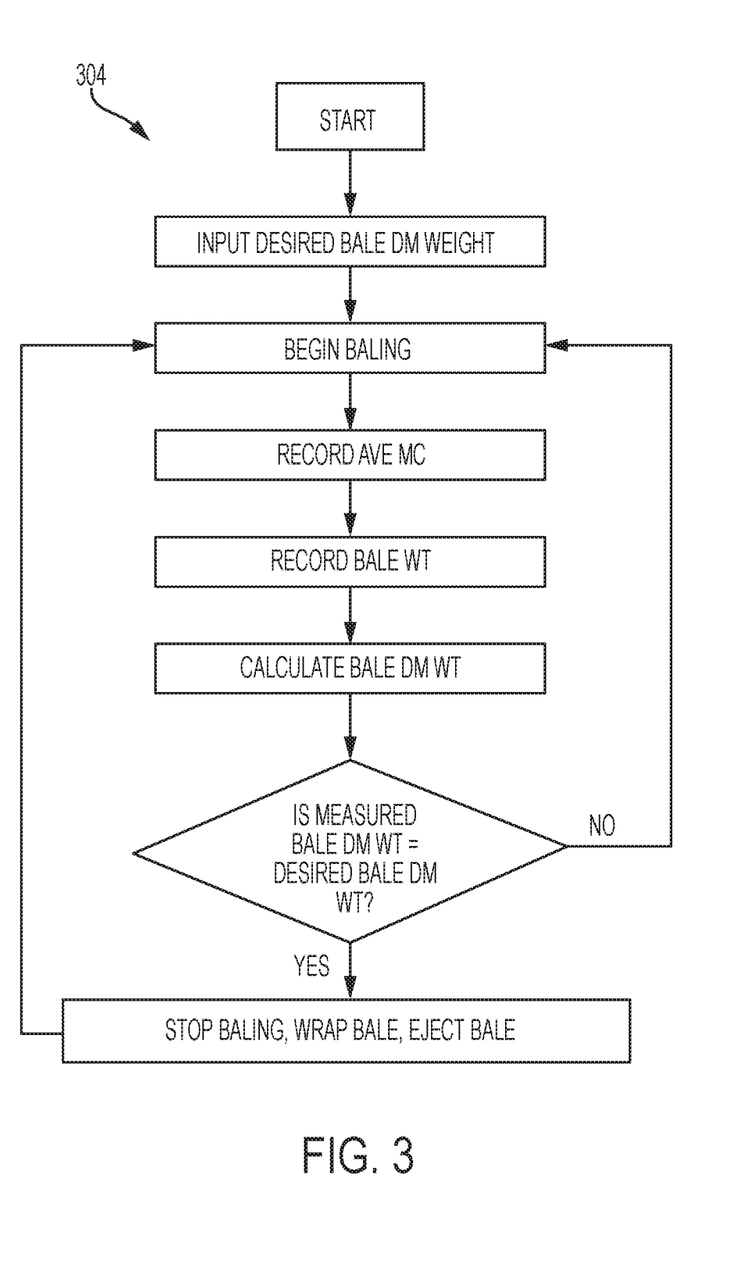
FIG. 3 is a diagram of a second mode of operation of the baler of FIG. 1.

Illustrated in FIGS. 1-3, the controller 34 of the baler 10 includes a processor 114, a memory unit 118 in operable communication with the processor 114, one or more sensors 122, 126, 130 sending and receiving signals from the processor 114, and a user interface 134 in operable communication with the processor 114. The processor 114 may also be in operable communication with various elements of the baler 10 such as the baler tension arm 94, the feed system 22, the discharge gate 46, and the like. During use, the processor 114 receives signals from the one or more sensors 122, 126, 130 and combines that information with one or more control algorithms to calculate the mass of DM contained in the currently forming bale 106 and/or the required dimensions (e.g., diameter) or mass of the bale 106 needed to achieve a desired amount of DM therein.

In particular, the baler 10 includes a bale-dimension sensor 122, a moisture sensor 126, and one or more mass sensors 130. The sensors 122, 126, 130, may be present individually, in plurality, or in combination. Although not illustrated, the processor 114 may also include additional sensors such as, but not limited to, a discharge gate position sensor and the like.

The bale-dimension sensor 122 includes a position sensor mounted to the tension arm 94 and configured to detect and output a signal representative of at least one dimension of the bale 106. More specifically, the bale-dimension sensor 122 outputs a signal representative of the bale diameter 110.

In the illustrated implementation, the bale-dimension sensor 122 detects the bale diameter 110 by monitoring the angular position of the tension arm 94 relative to the forward housing 42. However in alternative implementations, the sensor 122 may be mounted to other elements of the baler 10, such as the forward housing 42, the frame 14, and the like. Still further, in alternative implementations the bale-dimension sensor 122 may be any sensor type able to detect a dimension of the bale 106 either directly (e.g., by directly monitoring the bale itself) or indirectly (e.g., by monitoring the relative position of the tension arm 94 or other elements within the volume 50). Such sensors may include but are not limited to Hall Effect sensors, variable resistance sensors, optical sensors, and the like.

The moisture sensor 126 includes a sensor mounted to the baler 10 proximate the inlet 90 of the forming chamber 86 that is configured to output a signal representative of the moisture level of the crop material 30 entering the forming chamber 86. In the illustrated implementation, the moisture sensor 126 is mounted to the frame 14 proximate the inlet 90, however in alternative implementations, the moisture sensor 126 may be incorporated into the feed system 22, and the like. The moisture sensor 126 may be any type of sensor able to detect the moisture of the crop material 30 both directly and indirectly.

The one or more mass sensors 130 include a series of sensors that, together, are configured to detect the total mass of the bale 106. By way of example only, the mass sensors 130 may be positioned between and coupled to both the forward housing 42 and the frame 14. In such implementations, the mass sensors 130 may actually weigh the combined weight of the bale 106 and the elements of the bale forming system 26. In other implementations, the mass sensors 130 may be coupled to the tongue 54 of the frame 14 and/or to the wheels 18. In still other implementations, the mass sensors 130 may be attached to an auxiliary device (not shown) such as an accumulator, a wrapping device, a separate trailer, and the like. In such implementations, the mass sensors 130 may be configured to detect the mass of the bale 106 after it has been ejected from the bale forming system 26.

During the baling process, the processor 114 of the baler 10 receives information regarding the dimensions of the bale 106, the moisture content of the crop material 30 entering the forming chamber 86 and contained in the bale 106, and the total mass of the bale 106. Using the received information, the processor 114 is able to calculate 1) the current bale volume (BaleVol), 2) the average moisture content of the crop material 30 contained in the bale 106 (BaleMoist), and 3) the mass of DM contained within the bale 106 (DMMass). Using this information, the processor 114 provides signals to the user, via the user interface 134, indicating, among other things, when the desired mass of DM is contained in the bale 106, and/or the dimensions of the bale 106 needed to produce the desired mass of DM therein.

When operating, the processor 114 calculates the current bale volume (BaleVol) by inputting the current bale diameter (BaleDia), as detected by the bale-dimension sensor 122, and the known width of the forming chamber (ChamberWidth), pre-programmed into the memory 118, into the corresponding bale volume equation:

$$(BaleVol) = \left(\pi * \left(\frac{BaleDia}{2}\right)^2\right) * (ChamberWidth)$$

While the present implementation assumes a substantially cylindrical shaped bale, it is understood that the processor 114 may use different equations tailored to the particular shape and size of the bale being formed.

Furthermore, the processor 114 calculates the average moisture content of the crop material forming the bale 106 (BaleMoist). For the purposes of this application, the average moisture content of the bale (BaleMoist) is defined as the percentage of the mass of the bale 106 that is produced by water. In some implementations, the processor 114 calculates BaleMoist by compiling the running average of the moisture content detected in the crop material 30 fed into the forming chamber 86 over a pre-determined period of time, i.e., during the creation of the present bale 106. In other implementations, the processor 114 calculates BaleMoist by compiling the running average of the moisture content detected in the crop material 30 fed into the forming chamber 86 over the course of baling an entire field. In still other implementations, the processor 114 may take into account additional factors such as, but not limited to, the position within the field where the crop material 30 was collected, the elapsed time since the crop material 30 was collected, the geological attributes of the field, and the like.

Still further, the processor 114 calculates the total mass of the bale (BaleMass) by comparing weight readings provided by the one or more mass sensors 130 in two different configurations. More specifically, the processor 114 subtracts the mass reading of the baler 10 taken without a bale 106 positioned within the forming chamber 86 (BalerEmpty) from the weight reading taken with the bale 106 positioned in the forming chamber 86 (BalerFull). (BaleMass=BalerFull−BalerEmpty). In some embodiments, the processor 114 may re-calibrate the empty weight of the baler 10 (BalerEmpty) to compensate for changes in inclination, consumption of consumables (e.g., use of wrap material, loss of hydraulic fluid), and the like. In still other implementations, the mass sensors 130 may be positioned such that they more directly measure the weight of the bale 106, in such implementations the need to calibrate or calculate the total mass of the bale itself may be reduced. In still other implementations, the mass sensors 130 may be positioned on exterior devices (described above) such that the weight of those devices would need to be taken into account.

As illustrated in FIG. 2, a first operational mode 300 of the processor 114 begins with the user entering into the user interface 134 the mass of DM the user wants the bale 106 to contain (i.e., the Desired DM Mass or (DeDMMass)). The user also enters a target bale dimension the user estimates will contain the Desired DM Mass. In the present implementation, the target bale dimension is the bale diameter 110 (i.e., the User Diameter Estimate or (DiEst)).

With the initial information entered, the baler 10 begins the baling process. During the baling process, crop material 30 is collected from the support surface 58 by the feed system 22 and directed into the forming chamber 86 to form a bale 106 therein (described above). As the baling process proceeds, the processor 114 continuously receives signals from the bale-dimension sensor 122 and the moisture sensor 126. From this information, the processor 114 is able to continuously calculate the current bale volume (BaleVol) and the average moisture content of the crop material 30 contained in the bale 106 (BaleMoist).

For the first bale in the series, the baler 10 continues the baling process until the current bale includes a predetermined attribute, which in the first operational mode is a bale diameter 110 that is equal to the User Diameter Estimate (DiEst). Once achieved, the processor 114 stops the baling process by sending an appropriate signal to the user via the user interface 134. In alternative implementations, the predetermined attribute may also include, but is not limited to, a predetermined dimension, a predetermined total mass, a predetermined DM mass, and the like.

With the baling process stopped, the processor 114 then takes one or more readings using the mass sensors 130 to determine the bale's total mass (BaleMass; described above). Once weighed, the baler 10 wraps the bale 106 and ejects the bale from the forming chamber 86.

With the bale 106 ejected, the processor 114 calculates the mass of DM (DMMass) that was contained in the previous bale 106 by entering the calculated mass (BaleMass) and average moisture content (BaleMoist) into the following equation:

$$(DMMass) = (BaleMass) * (1 - (BaleMoist))$$

If the calculated mass of DM (DMMass) meets or exceeds the Desired DM Mass (DeDMMass), the processor 114 resumes the baling process and begins creation of a second bale 106 as described above (e.g., using the (DiEst) as the target bale size or predetermined attribute). However, if the calculated mass of DM in the bale 10 (DMMass) is below the Desired DM Mass (DeDMMass), the processor 114 calculates a new predetermined attribute or target bale diameter (TD) taking into consideration the newly acquired data. More specifically, the processor 114 calculates a new target diameter (TD) by entering the calculated mass of DM in the bale (DMMass), the calculated volume of the bale (BaleVol), and the desired mass (DeDMMass) into the following equation:

$$(TD) = 2\sqrt{\frac{(DeDMMass)*(BaleVol)}{(DMMass)*(ChamberWidth)*\pi}}$$

Simplified in view of the user inputs (e.g., the estimated bale dimension), the new target diameter (TD) can also be calculated using the following equation:

$$(TD) = \sqrt{\frac{(DeDMMass)*(DiEst)^2}{(DMMass)}}$$

Once calculated, the processor 114 replaces the Estimated Bale diameter with the new calculated Target Diameter (TD) and resets the baler 10 to begin forming a second bale. The processor 114 then resumes the baling process using the Target Diameter (TD), instead of the user diameter estimate (DiEst), as the predetermined attribute, as described above. The processor 114 will then re-evaluate the Target Diameter (TD) after each subsequent bale is created, adjusting the Target Diameter (TD) as necessary to adjust for changing crop conditions.

It is to be understood that while the first operational mode 304 indicates that the first bale 106 be ejected before the processor 114 calculates the mass of DM (DMMass) of said bale, in alternative implementations the calculations may occur with the bale 106 still positioned in the forming chamber 86. In such embodiments, if the bale 106 is found to contain a mass of DM (DMMass) that is less than the Desired DM Mass (DeDMMass), then the baler 106 may resume baling with the same bale 106 remaining in the forming chamber 86, thereby allowing the bale 106 to be enlarged until it achieves the newly calculated target diameter (TD). Still further, in some implementations, the processor 114 may be configured to update the target diameter (TD) anytime the calculated dry matter mass (DMMass) falls outside a pre-determined range, regardless of whether the mass is higher or lower than the desired DM Mass (DeDMMass).

As illustrated in FIG. 3, a second operational mode 304 of the processor 114 begins with the user entering into the user interface 134 the mass of DM the user wants the bale 106 to contain (i.e., the Desired DM Mass or (DeDMMass)).

With the initial information entered, the baler 10 begins the baling process. During the baling process, crop material 30 is collected from the support surface 58 by the feed system 22 and directed into the forming chamber 86 to form a bale 106 therein (described above). As the baling process proceeds, the processor 114 continuously receives signals from the one or more mass sensors 130 and the moisture sensor 126. From this information, the processor 114 is able to continuously calculate the current bale weight (BaleMass), the average moisture content of the crop material 30 contained in the bale 106 (BaleMoist), and the mass of DM contained in the current bale 106 (DMMass) using the equation below:

$$(DMMass) = (BaleMass) * (1 - (BaleMoist))$$

The baler 10 continues the baling process until the bale 106 includes the predetermined attribute, which in the second operational mode includes is a mass of DM contained in the bale 106 (DMMass) that is equal to the Desired DM Mass entered by the user (DeDMMass). Once achieved, the processor 114 stops the baling process by sending an appropriate signal to the user via the user interface 134. The baler 10 wraps the bale 106 and ejects the bale from the forming chamber 86. The baler 10 then resets and the process begins anew.

Figure 4:
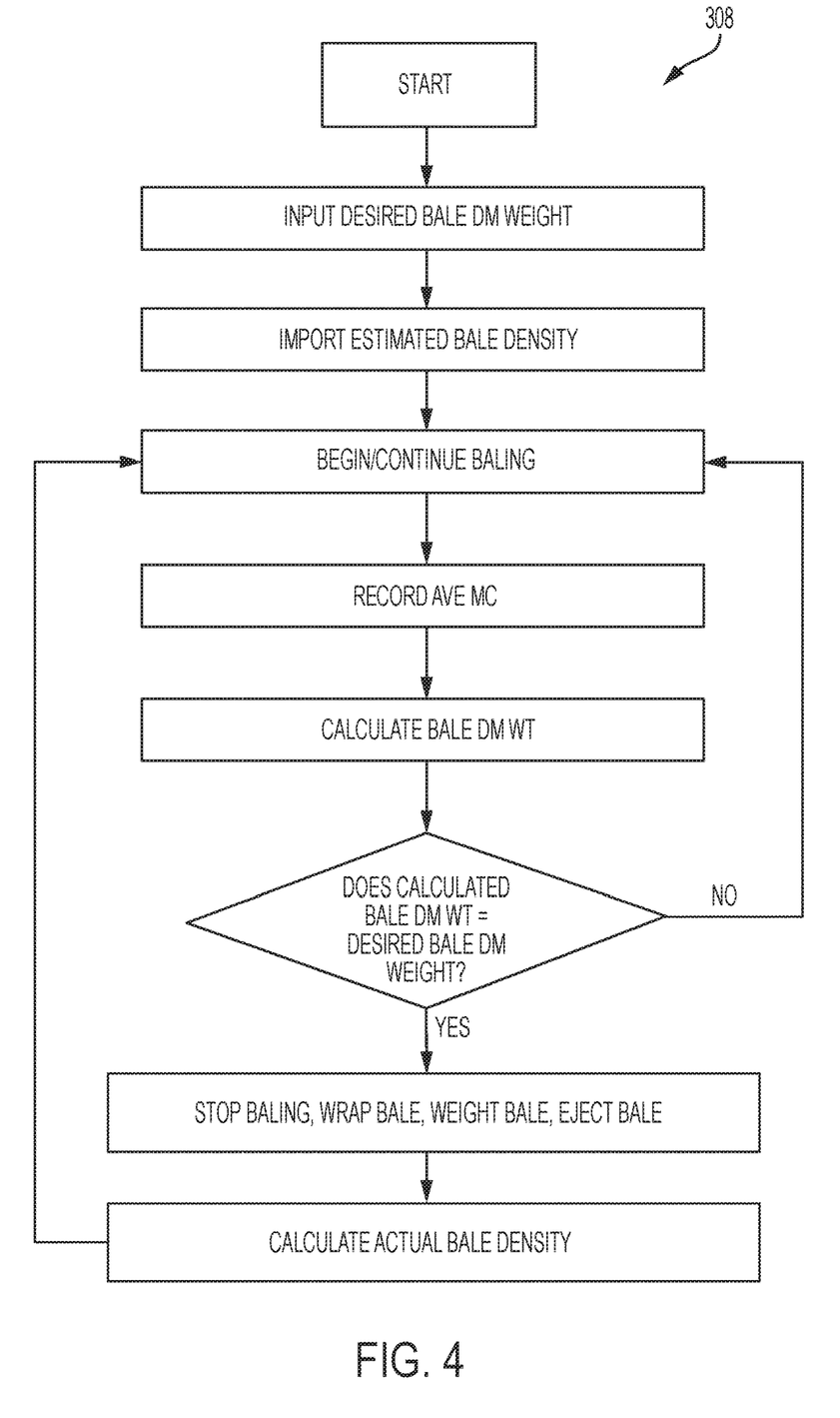
FIG. 4 is a diagram of a third mode of operation of the baler of FIG. 1.

As illustrated in FIG. 4, a third operational mode 308 of the processor 114 begins with the user entering into the user interface 134 the mass of DM the user wants the bale 106 to contain (i.e., the Desired DM Mass (DeDMMass)). The processor 114 also imports an estimated bale density (EsBDen). In the illustrated implementation, the estimated bale density (EsBDen) may be manually entered by the user or calculated from bales formed previously. In alternative implementations, the estimated bale density (EsBDen) may be drawn from a pre-calculated table taking into consideration, at least in part, the type of crop being baled, the type of baler being used, the weather, the anticipated moisture level in the crop material, and the like.

With the initial information entered, the baler 10 begins the baling process. During the baling process, crop material 30 is collected from the support surface 58 by the feed system 22 and directed into the forming chamber 86 to form a bale 106 therein (described above). As the baling process proceeds, the processor 114 continuously receives signals from the bale-dimension sensor 122 and the moisture sensor 126. From this information, the processor 114 is able to continuously determine the current bale volume (BaleVol), and the average moisture content of the crop material 30 contained in the bale 106 (BaleMoist) as described above.

Using the current bale volume (BaleVol), the average moisture content (BaleMoist), and the estimated bale density (EsBDen), the processor 114 is able to calculate an estimated DM Mass (EsDMMass) currently contained in the bale using the following equation:

(EsDMMass)=(BaleVol)*(EsBDen)*(1−(BaleMoist))

The baler 10 continues the baling process until the bale includes the predetermined attribute, which in the third operational mode includes an estimated mass of DM contained in the bale 106 (EsDMMass) that is equal to the Desired DM Mass (DeDMMass) entered by the user. Once achieved, the processor 114 stops the baling process by sending an appropriate signal to the user via the user interface 134. The baler 10 then weighs the bale 106 using the mass sensors 130, wraps the bale 106, and ejects the bale from the forming chamber 86. With the bale 106 ejected, the processor 114 then uses the measured bale mass (BaleMass) to calculate the actual bale density (ActBDen) using the following equation:

$$(ActBDen) = \frac{(BaleMass)}{(BaleVol)}$$

The processor 116 may then use the actual bale density (ActBDen) to update the estimated bale density (EsBDen). In doing so, the processor 116 may replace the estimated bale density (EsBDen) outright or may incorporate the new information into the estimated bale density (EsBDen) using an algorithm. With the estimated bale density updated, the baler 10 then resets and the process begins anew.

It is to be understood that while the third operational mode 304 ejects the bale 106 once the estimated mass of DM (EsDMMass) is equal to the Desired DM Mass (DeDMMass), in alternative implementations the processor 114 may weigh the bale (as described above) before it is ejected to update the estimated bale density (EsBDen) and to compare the estimated Bale mass (EsBaleMass) with the actual bale mass (EsBaleMass). In such implementations, the processor 114 may then adjust the estimated bale density (EsBDen) based on the actual bale density or increase the size of the bale 106 until the actual bale mass is equal to the Desired DM.

What is claimed is:

1. A system comprising:
a baler configured to produce a bale having a predetermined dimension;
a mass sensor configured to measure a total mass of the bale;
a bale-dimension sensor configured to measure a dimension of the bale;
a moisture sensor configured to measure a moisture content of the bale; and
a controller configured to:
calculate an actual dry matter mass of the bale;
compare a desired dry matter mass to the actual dry matter mass of the bale; and
adjust the predetermined dimension based at least in part on the comparison of the desired dry matter mass to the actual dry matter mass of the bale.

2. The system of claim 1, wherein the bale-dimension sensor is configured to measure a bale diameter.

3. The system of claim 1, wherein the predetermined dimension is adjusted based at least in part upon a ratio of the actual dry matter mass to the desired dry matter mass.

4. The system of claim 1, wherein the predetermined dimension is adjusted based at least in part on a density of the bale.

5. The system of claim 1, wherein the predetermined dimension is a bale diameter.

6. The system of claim 1, wherein the desired dry matter mass is input into the controller via a user interface.

7. The system of claim 1, wherein the actual dry matter mass of the bale is calculated based at least in part on the total mass of the bale and the moisture content of the bale.

8. A method of forming a bale with a baler having a controller, the method comprising:
receiving a signal indicating a moisture content of the bale;
receiving a signal indicating a total mass of the bale;
calculating an actual dry matter mass of the bale based at least in part on the moisture content of the bale and the total mass of the bale;
comparing the actual dry matter mass of the bale to a desired dry matter mass of the bale; and
adjusting a first attribute of the bale based at least in part on the comparison of the actual dry matter mass and the desired dry matter mass.

9. The method of claim 8, further comprising receiving a signal indicating at least one dimension of the bale.

10. The method of claim 9, wherein the first attribute is a predetermined dimension of the bale.

11. The method of claim 9, further comprising comparing the at least one dimension of the bale to a desired dimension of the bale.

12. The method of claim 8, wherein the first attribute is a predetermined mass of the bale.

13. A system comprising:
a baler configured to produce a bale having a predetermined attribute;
a force sensor configured to detect a total mass of the bale;
a moisture sensor configured to measure a moisture content of the bale; and
a controller configured to:
calculate an actual dry matter mass of the bale based at least in part on the total mass of the bale and the moisture content of the bale;
compare a desired dry matter mass to the actual dry matter mass; and
adjust the predetermined attribute for a successive bale based at least in part on the comparison of the desired dry matter mass and the actual dry matter mass.

14. The system of claim 13, wherein the predetermined attribute is a predetermined dimension or a predetermined mass.

* * * * *